United States Patent [19]

Römer et al.

[11] 4,400,293
[45] Aug. 23, 1983

[54] LIQUID CRYSTALLINE CYCLOHEXYLPHENYL DERIVATIVES

[75] Inventors: Michael Römer, Rodgau; Joachim Krause, Dieburg; Ludwig Pohl, Darmstadt, all of Fed. Rep. of Germany

[73] Assignee: Merck Patent Gesellschaft mit beschränkter Haftung, Darmstadt, Fed. Rep. of Germany

[21] Appl. No.: 316,382

[22] Filed: Oct. 29, 1981

[30] Foreign Application Priority Data

Oct. 29, 1980 [DE] Fed. Rep. of Germany ....... 3040632

[51] Int. Cl.³ .............. G02F 1/13; C09K 3/34; C07C 13/28; C07C 25/06; C07C 43/21; C07C 43/225; C07C 121/48; C07C 121/64; C07C 121/75

[52] U.S. Cl. ............. 252/299.63; 252/299.5; 350/350 R; 568/52; 568/56; 568/58; 568/631; 568/644; 568/645; 568/647; 570/129; 570/184; 585/20; 585/23; 585/25; 260/46 SC; 260/46 SF; 260/46 SG

[58] Field of Search ............ 252/299.63, 299.66, 252/299.65, 299.5; 260/46 SC, 46 SF, 46 SG; 350/350 R; 568/52, 54, 56, 58, 631, 644, 645, 647; 585/20, 23, 25; 570/129, 182, 184, 188

[56] References Cited

U.S. PATENT DOCUMENTS

| | | | |
|---|---|---|---|
| 4,035,056 | 7/1977 | Coates et al. | 252/299.66 |
| 4,154,697 | 5/1979 | Eidenschink et al. | 252/299.63 |
| 4,229,315 | 10/1980 | Krause et al. | 252/299.63 |
| 4,237,026 | 12/1980 | Eidenschink et al. | 252/299.63 |
| 4,261,651 | 4/1981 | Gray et al. | 252/299.63 |
| 4,330,426 | 5/1982 | Eidenschink et al. | 252/299.5 |
| 4,340,498 | 7/1982 | Sugimori | 252/299.63 |
| 4,357,078 | 11/1982 | Carr et al. | 252/299.63 |
| 4,361,494 | 11/1982 | Osman et al. | 252/299.63 |

FOREIGN PATENT DOCUMENTS

| | | | |
|---|---|---|---|
| 30761 | 6/1981 | European Pat. Off. | 252/299.63 |
| 56-138135 | 10/1981 | Japan | 252/299.6 |
| 56-140944 | 11/1981 | Japan | 252/299.63 |
| 57-5780 | 1/1982 | Japan | 252/299.63 |
| 57-54137 | 3/1982 | Japan | 252/299.63 |
| 57-59851 | 4/1982 | Japan | 252/299.63 |
| 57-95933 | 6/1982 | Japan | 252/299.63 |
| 2086385 | 5/1982 | United Kingdom | 252/299.63 |

OTHER PUBLICATIONS

Osman, M. A., Mol. Cryst. Liq. Cryst., vol. 72 (Letters), pp. 291-295 (1982).
Gray, G. W., Mol. Cryst. Liq. Cryst., vol. 63, pp. 3-18 (1981).
Gray, G. W., Mol. Cryst. Liq. Cryst., vol. 53, pp. 147-166 (1979).
Osman, M. A., Mol. Cryst. Liq. Cryst., vol. 82 (Letters), pp. 47-52 (1982).
Praefcke, K. et al., Chemiker-Zeitung, vol. 104, No. 9, pp. 269-271 (1980).

Primary Examiner—Teddy S. Gron
Attorney, Agent, or Firm—Millen & White

[57] ABSTRACT

Cyclohexylphenyl derivatives of the formula

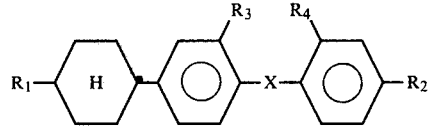

wherein X is —CH$_2$—CH$_2$—, —CH$_2$—O—, —CH$_2$—S—, —O—CH$_2$— or —S—CH$_2$—; R$_1$ is alkyl of up to 8 carbon atoms; R$_2$ is alkyl or alkoxy each of up to 8 carbon atoms, fluorine, chlorine, bromine or cyano; and R$_3$ and R$_4$ are both hydrogen or one is hydrogen and the other is fluorine, chlorine, bromine or cyano, with the proviso that R$_3$ and R$_4$ are both hydrogen when X is —CH$_2$—CH$_2$— or R$_2$ is fluorine, chlorine, bromine or cyano, are valuable liquid crystalline compounds.

11 Claims, No Drawings

LIQUID CRYSTALLINE CYCLOHEXYLPHENYL DERIVATIVES

BACKGROUND OF THE INVENTION

To a wide extent, for electro-optic indicator elements, the properties of nematic or nematic-cholesteric liquid crystalline materials are employed. These include significant changes in their optical properties, such as light absorption, light scattering, birefringence, reflectivity or color under the influence of electric fields. The function of such indicator elements thereby depends, for example, on the phenomena of dynamic scattering, the deformation of aligned phases, the Schadt-Helfrich effect in the twisted cell or the cholesteric-nematic phase transition.

For the technical use of these effects in electronic constructional elements, liquid crystalline dielectrics are needed which must satisfy a number of requirements. Especially important is chemical stability towards moisture, air and physical influences, such as heat, radiation in the infra-red, visible and ultra-violet ranges and direct and alternating electric fields. Furthermore, there is required of technically useable liquid crystalline dielectrics a liquid crystalline mesophase in the temperature range of at least $+10°$ C. to $+50°$ C., preferably of $0°$ C. to $60°$ C., and the lowest possible viscosity at room temperature, which is preferably not more than $70\times10^{-3}$ Pa.s. Finally, in the range of visible light, they are to have no inherent absorption, i.e., they must be colorless.

A number of liquid crystalline compounds is already known which satisfy the stability requirements demanded of dielectrics for electronic constructional elements and which are also colorless. Included, in particular, are the p,p'-disubstituted benzoic acid phenyl esters described in published Federal Republic of Germany Patent Application No. 2,139,628 and the p,p'-disubstituted phenylcyclohexane derivatives described in published Federal Republic of Germany Patent Application No. 2,636,684. In both mentioned classes of compounds, and also in other known series of compounds with a liquid crystalline mesophase, there is no individual compound which, in the required temperature range of $10°$ C. to $60°$ C., forms a liquid crystalline nematic mesophase. Therefore, as a rule, mixtures of two or more compounds are prepared in order to obtain substances useable as liquid crystalline dielectrics. For this purpose, one usually mixes at least one compound with low melting or clear point with another with distinctly higher melting and clear point. A mixture is thereby normally obtained, the melting point of which lies below that of the lower melting component, and whose clear point lies between the clear points in the components. Nevertheless, the preparation of optimal dielectrics still causes difficulties since the components with the high melting and clear points frequently also impart a high viscosity to the mixtures. The operating times of the electro-optical indicator elements produced using them are thereby prolonged in an undesirable manner. Furthermore, problems arise since often the solubility of the various components in one another, especially at room temperature or lower temperatures, is only very limited.

SUMMARY OF THE INVENTION

Accordingly, it is an object of this invention to provide liquid crystalline dielectrics which display a nematic phase in the required temperature range and permit sufficiently short operating times in liquid crystal cells at room temperature.

Upon further study of the specification and appended claims, further objects and advantages of this invention will become apparent to those skilled in the art.

These objects have been achieved by providing the cyclohexylphenyl derivatives of formula (I)

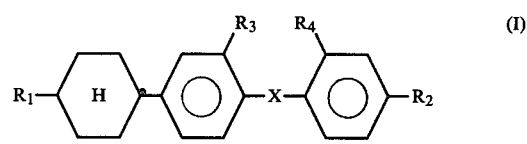

wherein X is $-CH_2-CH_2-$, $-CH_2-O-$, $-CH_2-S-$, $-O-CH_2-$ or $-S-CH_2-$; $R_1$ is alkyl of up to 8 carbon atoms, $R_2$ is alkyl or alkoxy each of up to 8 carbon atoms, fluorine, chlorine, bromine or cyano; and $R_3$ and $R_4$ each is hydrogen or one is hydrogen and the other fluorine, chlorine, bromine or cyano, with the proviso that $R_3$ and $R_4$ both are hydrogen when X is $-CH_2-CH_2-$ or $R_2$ is fluorine, chlorine, bromine or cyano.

They are excellently suited as components of liquid crystalline dielectrics. They possess an extra-ordinarily wide range of use: depending upon the selection of the substituents, the compounds of formula (I) can be used not only as base materials from which liquid crystalline dielectrics are exclusively or preponderantly composed, but compounds of formula (I) can also be added in smaller proportions of, for example, 2 to 45 weight percent, to liquid crystalline base materials of other classes of compounds in order to prepare dielectrics with a wider liquid crystalline mesophase or to influence the size of the dielectric anisotropy of such a dielectric.

By suitable selection of the substituents $R_1$ to $R_4$, the compounds of formula (I) can be used to produce not only dielectrics with outstandingly positive dielectric anisotropy for use in indicator elements based on the twisted nematic cell or of the cholesteric-nematic phase transition, but there can also be produced dielectrics, with dielectric anisotropies varying from only a very little different from zero also to negative values, which are used in indicator elements based on dynamic scattering or on the deformation of aligned phases (DAP effect).

In the pure state, the compounds of formula (I) are colorless and form nematic mesophases in an astonishingly broad temperature range which is favorably situated for their electro-optical use.

Thus, in one aspect this invention relates to the cyclohexylphenyl derivatives of formula (I) and their use as components of liquid crystalline dielectrics. In another aspect, this invention relates, furthermore, to liquid crystalline dielectrics containing at least one cyclohexylphenyl derivative of formula (I), as well as electro-optical indicator elements having a liquid crystal cell which contains such a liquid crystalline dielectric.

DETAILED DISCUSSION

The cyclohexylphenyl derivatives of this invention include the 1,2-diphenylethane derivatives of formula (Ia),

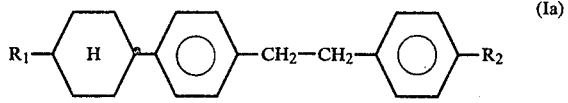

the 4-(trans-4-alkylcyclohexyl)-benzyl phenyl ethers of formula (Ib),

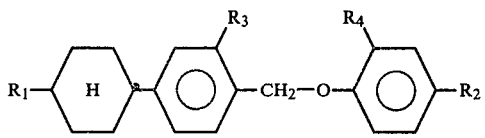

the 4-(trans-4-alkylcyclohexyl)-benzyl phenyl thioethers of formula (Ic),

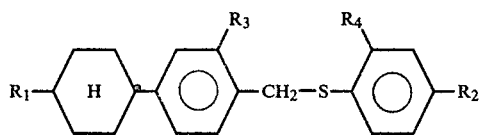

the benzyl-4-(trans-4-alkylcyclohexyl)-phenyl ethers of formula (Id),

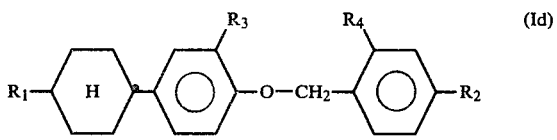

and the benzyl-4-(trans-4-alkylcyclohexyl)-phenyl thioethers of formula (Ie),

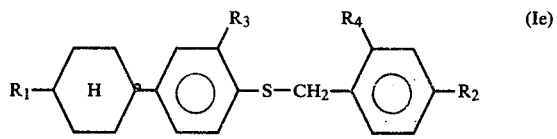

wherein $R_1$ to $R_4$ are as defined for formula (I).

Throughout, the trans-position of the substituents in the 1- and 4-positions of the cyclohexane ring is indicated in the structural formulae by a distinctive black spot on the right side of the ring.

The 1,2-diphenylethane derivatives of formula (Ia) have a dielectric anisotropy of around zero when the substituent $R_2$ is alkyl or alkoxy. If, on the other hand, $R_2$ is fluorine, chlorine, bromine or cyano, these compounds of formula (Ia) have a distinctly positive dielectric anisotropy; these materials, especially those in which $R_2$ is fluorine or cyano, are mainly used for indicator elements based on the twisted cell.

In the ether or thioether derivatives of formulae (Ib) to (Ie), when $R_3$ and $R_4$ are hydrogen, the dielectric anisotropy variations are similar to those of the correspondingly substituted compounds of formula (Ia). If, however, in a compound of the formulae (Ib) to (Ie), $R_3$ or $R_4$ is fluorine, chlorine, bromine or cyano and $R_2$ is accordingly an alkyl or alkoxy group, these compounds have, as a rule, a negative dielectric anisotropy; they are, therefore, preferably used in dielectrics for indicator elements based on dynamic scattering. In the benzyl ether or benzyl thioether derivatives of the formulae (Ib) to (Ie), the substituent $R_3$ and $R_4$ which is in the position ortho to the benzylic methylene group is preferably always a hydrogen atom.

In the compounds of formula (I), the alkyl groups for $R_1$, as well as the alkyl or alkoxy groups for $R_2$, can be straight-chained or branched. When these are straight-chained, i.e., methyl, ethyl, n-propyl, n-butyl, n-pentyl, n-hexyl, n-heptyl or n-octyl, the thereby characterized compounds as a rule possess higher clear points than those with branched side chain groups $R_1$ and/or $R_2$. Consequently, usually at most one of the side chain groups $R_1$ and $R_2$ is branched. Compounds of formula (I) with a branched side chain group $R_1$ or $R_2$ are sometimes of importance because of a better solubility in the usual liquid crystalline base materials but especially as chiral doping agents if, due to the chain branching, they possess optical activity. Such branched side chain groups generally contain not more than one chain branching. Preferred branched hydrocarbon radicals R are those in which, on a comparatively long carbon chain, a methyl or ethyl group is present in the 1-, 2- or 3-position, for example 2-methylpropyl, 2-methylbutyl, 3-methylbutyl, 2-methylpentyl, 3-methylpentyl, 2-ethylhexyl or 1-methylhexyl. When $R_2$ is alkyl or alkoxy, the side chain groups $R_1$ and $R_2$ together contain up to 16 carbon atoms. In the scope of the present invention, among these are preferred those in which $R_1$ and $R_2$ together contain 3 to 13, especially 4 to 11 carbon atoms.

The compounds of this invention are prepared in conventional manner for such substances. Thus, for example, the 1-[4-(trans-4-alkylcyclohexyl)-phenyl]-2-(4-$R_2$-phenyl)ethanes of formula (Ia) are obtained by reducing a compound of formula (II)

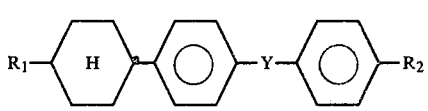

wherein Y is —$CH_2$—CO—, —CO—$CH_2$— or —CH=CH— and $R_1$ and $R_2$ are as defined for formula (I), in per se known manner, for example by catalytic hydrogenation. Suitable catalysts preferably include a finely-divided platinum group metal, for example palladium precipitated onto active charcoal. Such hydrogenations can be carried out by passing hydrogen into a solution of the compound of formula (II) at room temperature and normal pressure; as solvents, expediently used are those which, under these conditions, do not themselves react, for example, lower alcohols, such as ethanol, or aromatic hydrocarbons, such as toluene. The starting compounds of formula (II) can be prepared in per se known manner. For example, the benzyl ketones (II, Y=—CO—$CH_2$— or —$CH_2$—CO—) can be prepared by a Friedel-Crafts reaction from a 4-(trans-4-alkylcyclohexyl)-phenylacetic acid halide and an $R_2$-benzene or from a 4-$R_2$-phenylacetic acid halide and a (trans-4-alkylcyclohexyl)-benzene; the stilbenes (II, Y=—CH=CH—) can be obtained by the reaction of a 4-(trans-4-alkylcyclohexyl)-benzyl magnesium halide with a 4-$R_2$-benzaldehyde, followed by hydrolysis and splitting off of water.

The benzyl ethers or benzyl thioethers of the formulae (Ib) to (Ie) are prepared by reacting a compound of formula (III)

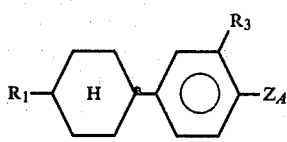

wherein $Z_A$ is OH, OMe, SH, SMe or —CH$_2$—Hal, where Me is one equivalent of a metal cation and Hal is a halogen atom, preferably chlorine or bromine, in the presence of a base with a compound of formula (IV)

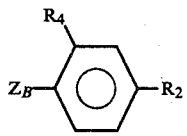

wherein $Z_B$ is —CH$_2$—Hal, when $Z_A$ is OH, OMe, SH or SMe, and signifies OH, OMe, SH or SMe, when $Z_A$ is —CH$_2$—Hal. The residues $R_1$ to $R_4$ in the compounds of formulae (III) and (IV) are as defined for formula (I).

The reaction conditions for these ether or thioether syntheses from the compounds of formulae (III) and (IV) are fully conventional for such reactions. As solvents there can be used polar, aprotic compounds, for example dimethyl sulfoxide, N,N-dimethylformamide or N-methylpyrrolidone; preferred bases include alkali metal salts of weak acids, for example sodium acetate, potassium carbonate or sodium carbonate. The reactions can be carried out at temperatures of 0° C. to the boiling point of the lowest boiling component of the reaction mixture; it has proved to be especially advantageous to employ temperatures of 60° to 120° C.

Some of the starting materials of the formulae (III) and (IV) are known; in part, they can be prepared analogously to known compounds by standard processes of synthetic organic chemistry. Thus, the phenols of formulae (III) or (IV) ($Z_A$, $Z_B$=OH) are known when $R_3$ and $R_4$ are hydrogen; the corresponding o-chloro- or o-bromophenols are prepared by simple nuclear halogenation of these phenols. The o-cyanophenols can be prepared by the reaction of the o-bromophenols with copper(I) cyanide in pyridine. Finally, the o-fluorophenols are obtained by nitrating a phenol protected on the hydroxyl group, e.g., an acetylphenol, and subsequently reducing it to the o-aminoacetylphenol in which the amino group is then exchanged for a fluorine atom by diazotization in the presence of a tetrafluoroborate and thermal decomposition of the diazonium tetrafluoroborate. The benzyl halides, preferably benzyl chlorides of formula (III) or (IV) ($Z_A$, $Z_B$=CH$_2$Cl) are prepared in an equally conventional manner by reacting the corresponding benzene derivative with paraformaldehyde and hydrogen chloride in the presence of hydrochloric acid. Finally, the thiophenols of formulae (III) or (IV) are obtained either by reducing the corresponding sulfochlorides or converting the corresponding phenols into the thiophenols by esterification with dimethylthionocarbamoyl chloride, isomerizing the product to the dimethylthiocarbamic acid S-phenyl ester and subsequently hydrolytically splitting the product.

The liquid crystalline dielectrics of this invention comprise two or more components, including at least one of formula (I); however, dielectrics of this invention can exclusively contain compounds of formula (I)—apart from additionally present optional doping or additive materials, which themselves need not necessarily be liquid crystalline. Further components optionally employed are preferably nematic or nematogenic substances from the classes of the azobenzene, azoxybenzenes, biphenyls, possibly partly hydrogenated terphenyls or quaterphenyls, Schiff bases, especially benzylidene derivatives, phenyl benzoates, phenylpyrimidines, phenylcyclohexanes, possibly halogenated stilbenes, diphenylacetylene derivatives, diphenyl nitrones, phenyl- or cyclohexylnaphthalenes, which can also be partly hydrogenated in the naphthalene part or contain nitrogen atoms, as well as substituted cinnamic acids. The most important compounds as such further components can be characterized by formula (V)

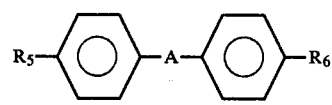

wherein A is

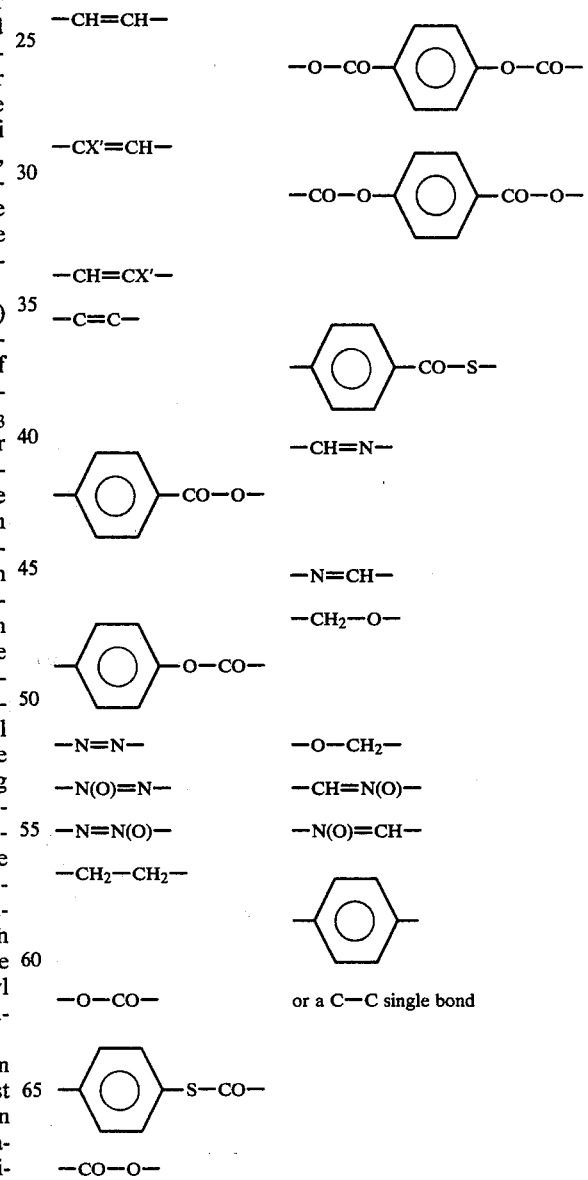

—S—CO—

—CO—S—

Other possible components of the dielectrics of this invention are those compounds of formula (V) in which one or more phenyl rings are replaced by a corresponding number of trans-cyclohexyl rings; furthermore, one of these rings can also be a 2,5-disubstituted pyrimidine ring, or a possibly partly hydrogenated 2,6-disubstituted naphthalene or quinazoline system.

X' is halogen, preferably Cl, or —CN. $R_5$ and $R_6$ are the same or different and can be alkyl, alkoxy, alkanoyl, alkanoyloxy or alkoxycarbonyloxy radicals of up to 18, preferably up to 8 C-atoms; furthermore, one of these radicals can also be trans-4-alkylcyclohexyl, —CN, —NC, $NO_2$, $CF_3$ or halogen.

In the case of most of these compounds, $R_5$ and $R_6$ are preferably different, and one of the residues usually is alkyl or alkoxy. However, a large number of other variants of the intended substituents are also conventional. Many such substances are commercially available.

As a rule, the dielectrics of this invention contain at least 30, preferably 50–99, especially 60–98 percent by weight of the compounds of formula (I) and possibly (V). Of this, preferably at least 5 percent by weight, usually 10 or more percent by weight, e.g., 10–80% by weight is one or more compounds of formula (I).

The invention also includes those liquid crystalline dielectrics to which have been added, for example for doping purposes, less than 5 percent by weight, for example 0.1 to 3 parts by weight of one or more compounds of formula (I).

The preparation of the dielectrics of this invention is carried out in per se conventional manner. As a rule, the desired amount of the components used in lesser amount is dissolved in the components making up the main component, expediently at an elevated temperature. When a temperature above the clear point of the main component is thereby chosen, the completeness of the dissolving procedure can be observed especially easily.

However, it is also possible to mix solutions of the components of formula (I) and possibly (V) in a suitable organic solvent, for example acetone, chloroform or methanol, and then to remove the solvent after thorough mixing, for example by distillation under reduced pressure. Of course, in the case of this process method, care must be taken that no impurities or undesired doping materials are entrained by the solvent.

By means of suitable additives, the liquid crystalline dielectrics of this invention can be so modified that they can be employed in all previously known kinds of liquid crystal indicator elements. Such additives are known to the expert and are described in detail in the appropriate literature. For example, substances can be added to change the dielectric anisotropy, the optical anisotropy, the viscosity, the conductivity and/or the orientation of the nematic phases. Such substances are described, for example, in published Federal Republic of Germany Patent Applications Nos. 22 09 127, 22 40 864, 23 21 632, 23 38 281, 25 35 046, 26 37 430, 27 02 598, 29 00 312 and 30 00 375.

Without further elaboratiion, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the Examples, m.p. means melting point and K the clear point of a liquid crystalline substance in degrees Celsius; boiling temperatures are indicated by b.p.

EXAMPLE 1

(a) A solution of 61 g of 4-(trans-4-n-propylcyclohexyl)-acetophenone in 350 ml of ethanol is mixed with a solution of 28 g of hydroxylammonium chloride in 460 ml of water and the mixture, after the addition of a solution of 39 g of potassium hydroxide in 39 ml of water, is heated to the boil under reflux for 2 hours. After cooling, the reaction mixture is diluted with 2 l of cold water, the precipitated 4-(trans-4-n-propylcyclohexyl)-acetophenone oxime is filtered off, washed with water and dried in a vacuum for 24 hours at 90° C.; yield 67 g.

(b) 130 g of 4-(trans-4-n-propylcyclohexyl)-acetophenone oxime is introduced portionwise into a suspension of 125 g of phosphorus pentachloride in 500 ml of dichloromethane, with stirring and cooling to 20°–25°. After subsequent stirring for two hours, the reaction mixture is mixed with 1000 ml of water and the dichloromethane distilled off azeotropically. Subsequently, the reaction mixture is mixed with 250 ml of 37% aqueous hydrochloric acid and heated to the boil for one hour. Afer cooling to 20°, the precipitated 4-(trans-4-n-propylcyclohexyl)-aniline hydrochloride is filtered off, washed with water and dried; yield 120 g.

(c) 76 g of 4-(trans-4-n-propylcyclohexyl)-aniline hydrochloride is suspended in a mixture of 350 ml of water and 60 g of concentrated sulphuric acid. A solution of 21 g of sodium nitrite in 120 ml of water is slowly added dropwise, with stirring, in the temperature range of 0° to 5° and the reaction mixture then subsequently stirred for 1 hour. It is subsequently mixed with 450 ml of methanol and slowly heated to 70°. After cessation of the gas evolution, it is again cooled to 0°, the precipitate 4-(trans-4-n-propylcyclohexyl)-phenol is filtered off, dried and recrystallized from methanol; yield 35 g.

(d) A mixture of 11 g of 4-(trans-4-n-propylcyclohexyl)-phenol, 9.8 g of 4-cyanobenzyl bromide, 7.6 g of potassium carbonate and 50 ml of dimethylformamide is heated to 85° for 8 hours. After cooling, the reaction mixture is diluted with 100 ml of water and extracted in 3 portions with a total of 200 ml of dichloromethane. The combined extracts are washed with water, dried over sodium sulphate and evaporated. The 4-(trans-4-n-propylcyclohexyl)-phenyl-(4-cyanobenzyl)ether remaining behind is recrystallized from ethanol; m.p. 93°; K 138°, dielectric anisotropy $\Delta\epsilon = +16.8$.

There are prepared analogously:
4-(trans-4-ethylcyclohexyl)-phenyl-(4-cyanobenzyl)-ether,
4-(trans-4-n-hexylcyclohexyl)-phenyl-(4-cyanobenzyl)-ether,
4-(trans-4-n-propylcyclohexyl)-phenyl-(4-fluorobenzyl)-ether,
4-(trans-4-pentylcyclohexyl)-phenyl-(4-fluorobenzyl)-ether,
4-(trans-4-methylcyclohexyl)-phenyl-(4-n-pentyloxybenzyl)-ether, 4-(trans-4-n-butylcyclohexyl)-phenyl-(4-ethoxybenzyl)-ether, 4-(trans-4-n-heptylcyclohexyl)-phenyl-(4-ethylbenzyl)-ether, and 4-(trans-4-ethylcyclohexyl)-phenyl-(4-n-hexylbenzyl)-ether.

EXAMPLE 2

(a) 33 g of 4-(trans-4-n-propylcyclohexyl)-benzenesulphochloride is added portionwise to a suspension of 36 g of zinc dust in 100 ml of water at 50°, with stirring, in such a manner that the temperature of the reaction mixture does not exceed 60°. After completion of the addition of the sulphochloride, a further 5 g of zinc dust is added thereto and the reaction mixture heated for 10 minutes to 70°. After cooling to 15°, a solution of 250 g of 37% aqueous hydrochloric acid in 100 ml of water is added dropwise and the reaction mixture stirred overnight at room temperature. Subsequently, a further 25 g of zinc dust is added thereto and the mixture heated to the boil for 4 hours. After cooling, the 4-(trans-4-n-propylcyclohexyl)-thiophenol is extracted with ether; the extracts are washed with water, dried over sodium sulphate and evaporated, and the thiophenol remaining behind is distilled in a vacuum; b.p. 196°/0.05 m bar.

(b) Hydrogen chloride gas is passed into a mixture of 9.6 g of paraformaldehyde and 40 ml of 37% aqueous hydrochloric acid up to the formation of a clear solution. Subsequently, a solution of 30 g of n-butyloxybenzene in 20 ml of benzene is added dropwise at 15°–20° and the reaction mixture stirred for 4 hours at this temperature. The organic phase is separated off, washed twice with 30 ml amounts of water, dried and distilled. After distilling off the benzene, there is obtained 27 g of 4-n-butyloxybenzyl chloride; b.p. 102°/1 m bar.

(c) Analogously to Example 1(d), from 23 g of 4-(trans-4-n-propylcyclohexyl)-thiophenol and 20 g of 4-n-butyloxybenzyl chloride, there is obtained 31 g of 4-(trans-4-n-propylcyclohexyl)-phenyl-(4-n-butyloxybenzyl)thioether.

There are prepared analogously:
4-(trans-4-n-propylcyclohexyl)-phenyl-(4-ethoxybenzyl)thioether,
4-(trans-4-ethylcyclohexyl)-phenyl-(4-n-butyloxybenzyl)thioether,
4-(trans-4-methylcyclohexyl)-phenyl-(4-n-hexyloxybenzyl)thioether,
4-(trans-4-n-butylcyclohexyl)-phenyl-(4-n-butylbenzyl)thioether,
4-(trans-4-n-hexylcyclohexyl)-phenyl-(4-methylbenzyl)thioether,
4-trans-4-n-pentylcyclohexyl)-phenyl-(4-fluorobenzyl)thioether,
4-(trans-4-n-propylcyclohexyl)-phenyl-(4-fluorobenzyl)thioether,
4-(trans-4-n-butylcyclohexyl)-phenyl-(4-chlorobenzyl)thioether,
4-(trans-4-ethylcyclohexyl)-phenyl-(4-bromobenzyl)thioether,
4-(trans-4-n-propylcyclohexyl)-phenyl-(4-cyanobenzyl)thioether, and
4-(trans-4-n-pentylcyclohexyl)-phenyl-(4-cyanobenzyl)thioether.

EXAMPLE 3

A suspension of 11 g of 4-(trans-4-n-propylcyclohexyl)-phenol in 80 ml of dichloromethane is mixed dropwise at 0° with a solution of 8 g of bromine in 20 ml of dichloromethane. Subsequently, the mixture is stirred for 1 hr and mixed with 200 ml of water. The organic phase is separated off, washed with dilute sodium bisulphite solution, dried over sodium sulphate and evaporated in a vacuum. The 4-(trans-4-n-propylcyclohexyl)-2-bromophenol remaining behind is heated for 3 hrs at 95° with a 4-methoxybenzyl chloride, 7.6 g of potassium carbonate and 50 ml of dimethylformamide. After cooling, one dilutes with 100 ml of water and extracts with 150 ml of dichloromethane. The combined dichloromethane extracts are washed with water and evaporated in a vacuum. The 4-(trans-4-n-propylcyclohexyl)-2-bromophenyl-(4-methoxybenzyl) ether remaining behind is recrystallized from ethanol; m.p. 65°, K 74.5°; $\Delta\epsilon = -2.3$.

There are prepared analogously:
4-(trans-4-n-butylcyclohexyl)-2-bromophenyl-(4-n-butylbenzyl)ether,
4-(trans-4-n-butylcyclohexyl)-2-chlorophenyl-(4-n-hexyloxybenzyl)ether, and
4-(trans-4-ethycyclohexyl)-2-chlorophenyl-(4-n-hexylbenzyl)ether.

EXAMPLE 4

(a) 61 g of 4-(trans-4-n-propylcyclohexyl)-2-bromophenyl is dissolved in 200 ml of toluene and the solution is heated with 25 g of acetic acid anhydride, with the addition of 1 ml of concentrated sulphuric acid, for 2 hrs. at the boil. The reaction mixture is washed neutral with aqueous sodium hydrogen carbonate solution, dried over sodium sulphate and evaporated. The 4-(trans-4-n-propylcyclohexyl)-2-bromophenyl acetate remaining behind is recrystallized from ethanol; yield 65.9 g.

(b) 65 g of 4-(trans-4-n-propylcyclohexyl)-2-bromophenyl acetate and 18 g of copper (I) cyanide are heated to 160° C. for 2 hours in 360 ml of a mixture of pyridine and N-methyl-pyrrolidone (2:1). After cooling, a solution of 250 g of iron trichloride hexahydrate in 1.2 l of 20% hydrochloric acid is added thereto, the mixture is heated, with stirring, to 70° C. and, after cooling, extracted 5 times with 400 ml amounts of diethyl ether. The extracts are washed with aqueous sodium hydrogen carbonate solution and water, dried over sodium sulphate and evaporated. The 4-(trans-4-n-propylcyclohexyl)-2-cyanophenyl acetate remaining behind is recrystallized from ethanol; yield: 34 g.

(c) 34 g of 4-(trans-4-n-propylcyclohexyl)-2-cyanophenyl acetate is heated to the boil for 30 minutes with 150 ml of 10% aqueous potassium hydroxide solution. The mixture is then acidified with dilute hydrochloric acid, the precipitated 4-(trans-4-n-propylcyclohexyl)-2-cyano-phenol is filtered off and recrystallized from methanol; yield: 28.5 g.

(d) 28 g of (trans-4-n-propylcyclohexyl)-2-cyanophenol is etherified, analogously to Example 1(d), with 26.4 g of 4-n-propyloxybenzyl bromide; 39 g of 4-(trans-4-n-propylcyclohexyl)-2-cyanophenyl(4-n-propyloxybenzyl)ether is obtained.

There are prepared analogously:
4-(trans-4-ethylcyclohexyl)-2-cyanophenyl-(4-n-heptylbenzyl)ether, and
4-(trans-4-n-pentylcyclohexyl)-2-cyanophenyl-(4-ethylbenzyl)ether.

EXAMPLE 5

31.5 g of 4-(trans-4-n-propylcyclohexyl)-2-bromothiophenol [prepared from 4-(trans-4-n-propylcyclohexyl)-2-bromophenol obtained according to Example 3 by reaction with dimethylthiocarbamoyl chloride, thermal rearrangement and hydrolysis analogously to Organic Syntheses, Volume 51 (1971), pages 139–142] is etherified with 21.5 g of 4-ethoxybenzyl bromide analogously to Example 1(d). There is obtained 40.2 g of 4-(trans-4-n-propylcyclohexyl)-2-bromophenyl-(4-ethoxybenzyl)-thioether.

There are prepared analogously:
4-(trans-4-n-pentylcyclohexyl)-2-bromophenyl-(4-ethylbenzyl)thioether,
4-(trans-4-n-hexylcyclohexyl)-2-chlorophenyl-(4-n-propylbenzyl)thioether,
4-(trans-4-methylcyclohexyl)-2-chlorophenyl-(4-n-hexyloxybenzyl)thioether,
4-(trans-4-ethylcyclohexyl)-2-fluorophenyl-(4-n-pentylbenzyl)thioether,
4-(trans-4-n-propylcyclohexyl)-2-fluorophenyl-(4-n-butyloxybenzyl)thioether,
4-(trans-4-n-propylcyclohexyl)-2-cyanophenyl-(4-n-butyloxybenzyl)thioether,
4-(trans-4-n-butylcyclohexyl)-2-cyanophenyl-(4-n-pentylbenzyl)thioether, and
4-(trans-4-n-heptylcyclohexyl)-2-cyanophenyl-(4-ethylbenzyl)thioether.

EXAMPLE 6

(a) A solution of 23.2 g of 4-(trans-4-n-propylcyclohexyl)-phenol in 300 ml of chloroform is mixed portionwise, with stirring, with 30 ml of 65% aqueous nitric acid in such a manner that the temperature thereby does not increase above 15°. Subsequently, 200 ml of water is added thereto, the organic phase is separated off and evaporated under reduced pressure. The 4-(trans-4-n-propyl-cyclohexyl)-2-nitrophenol remaining behind is suspended in 250 ml of 5% aqueous ammonia solution and slowly added to a solution of 75 g of sodium dithionite in 250 ml of water. The reaction mixture is stirred for 2 hours at room temperature and then extracted three times with 150 ml amounts of toluene. The extract is evaporated and the 4-(trans-4-n-propylcyclohexyl)-2-aminophenol remaining behind is recrystallized from methanol; yield 7.2 g.

(b) 116.5 g of 4-(trans-4-n-propylcyclohexyl)-2-amino-phenol, 80 g of potassium carbonate and 110 g of benzyl bromide are heated to 100° for 10 seconds in 500 ml of N,N-dimethyl-formamide. Subsequently, the reaction mixture is poured into 1 l of water. From the mixture obtained, the 4-(trans-4-n-propylcyclohexyl)-2-aminophenyl benzyl ether formed is extracted with dichloromethane and, after distilling off of the extraction agent, is recrystallized from isopropanol; yield 120 g.

(c) 81 g of 4-(trans-4-n-propylcyclohexyl)-2-aminophenyl benzyl ether is dissolved in a mixture of 100 ml of 42% aqueous tetrafluoroboric acid and 100 ml of water and the solution mixed, with cooling to 5°–10°, with a solution of 17.3 g of sodium nitrite in 35 ml of water. After subsequent stirring for one hour, it is cooled to 0°, the 4-(trans-4-n-propylcyclohexyl)-1-benzyloxy-2-diazonium fluoroborate which crystallizes out is filtered off, washed with 40 ml of cold 5% aqueous tetrafluoroboric acid, 50 ml of cold methanol and 200 ml of diethyl ether and dried at room temperature under reduced pressure; yield 135 g.

(d) To a suspension of 9.9 g of sodium fluoride in 200 ml of 1,2,4-trichlorobenzene there is added, with stirring at 145°–150°, a suspension of 211 g of 4-(trans-4-n-propyl-cyclohexyl)-1-benzyloxy-2-diazonium tetrafluoroborate and 39.6 g of sodium fluoride in 600 ml of 1,2,4-trichlorobenzene in the course of 50 minutes. After subsequent stirring for 15 minutes, it is cooled to 40°, filtered and the filtered off salts washed with toluene. The filtrate is extracted with toluene, the extracts are combined with the wash liquid, the combined toluene phases are washed with water, dried and evaporated; as residue there remain 82 g of 4-(trans-4-n-propylcyclohexyl)-2-fluorophenyl benzyl ether.

(e) 40 g of 4-(trans-4-n-propylcyclohexyl)-2-fluorophenyl benzyl ether and 33 g of pyridine hydrochloride are heated for 1 hour at 200°–220°. After cooling, the comminuted reaction mass is taken up in 200 ml of water and this mixture extracted with toluene. The extracts are dried over sodium sulphate and evaporated; the 4-(trans-4-n-propyl-cyclohexyl)-2-fluorophenol remaining behind is recrystallized from methanol; yield 21 g.

(f) 11.8 g of 4-(trans-4-n-propylcyclohexyl)-2-fluorophenol is etherified with 11 g of 4-n-propylbenzyl bromide analogously to Example 1(d). There is obtained 14.1 g of 4-(trans-4-n-propyl-cyclohexyl)-2-fluorophenyl-(4-n-propylbenzyl)ether; m.p. 38°, K 84°.

There are prepared analogously:
4-(trans-4-n-butylcyclohexyl)-2-fluorophenyl-(4-ethylbenzyl)ether,
4-(trans-4-n-pentylcyclohexyl)-2-fluorophenyl-(4-n-propylbenzyl)ether,
4-(trans-4-ethylcyclohexyl)-2-fluorophenyl-(4-n-pentylbenzyl)ether, and
4-(trans-4-methylcyclohexyl)-2-fluorophenyl-(4-n-butyloxybenzyl)ether.

EXAMPLE 7

(a) Into a mixture of 20 g of 85% phosphoric acid, 40 ml of 36.5% aqueous hydrochloric acid and 9 g of paraformaldehyde there is passed hydrogen chloride gas, with ice cooling. To this is added dropwise at 0°, while stirring, a solution of 40 g of trans-4-n-butylphenylcyclohexane in 50 ml of glacial acetic acid and the reaction mixture subsequently stirred for 5 hours at room temperature. The reaction mixture is subsequently heated to the boil under reflux for 20 hours and, after cooling, poured onto 200 g of ice. The mixture obtained is extracted three times with 150 ml amounts of diethyl ether, the ether extracts are washed neutral with 5% aqueous sodium hydrogen carbonate solution, dried over potassium carbonate and evaporated. The 4-(trans-4-n-butylcyclohexyl)-benzyl chloride remaining behind is purified by distillation under reduced pressure; b.p. 164°/1 mb, yield: 28.5 g.

(b) From 26.4 g of 4-(trans-4-n-butylcyclohexyl)-benzyl chloride and 15 g of 4-n-butylphenol are obtained, analogously to Example 1(d), 4-(trans-4-n-butylcyclohexyl)-benzyl-(4-n-butylphenyl)ether; m.p. 47°, K. 102°.

There are prepared analogously:
4-(trans-4-n-heptylcyclohexyl)-benzyl-(4-methylphenyl)ether,
4-(trans-4-ethylcyclohexyl)-benzyl-(4-n-pentylphenyl)ether,
4-(trans-4-n-pentylcyclohexyl)-benzyl-(4-hexyloxyphenyl)ether,
4-(trans-4-n-pentylcyclohexyl)-benzyl-(4-n-butyloxyphenyl)ether,
4-(trans-4-n-hexylcyclohexyl)-benzyl-(4-bromophenyl)ether, 4-(trans-4-n-butylcyclohexyl)-benzyl-(4-chlorophenyl)ether,
4-(trans-4-n-propylcyclohexyl)-benzyl-(4-fluorophenyl)ether,
4-(trans-4-n-pentylcyclohexyl)-benzyl-(4-fluorophenyl)ether,
4-(trans-4-ethylcyclohexyl)-benzyl-(4-cyanophenyl)ether,
4-(trans-4-n-hexylcyclohexyl)-benzyl-(4-cyanophenyl)ether,
4-(trans-4-n-heptylcyclohexyl)-benzyl-(2-bromo-4-methoxyphenyl)ether,
4-(trans-4-ethylcyclohexyl)-benzyl-(2-bromo-4-n-heptylphenyl)ether,
4-(trans-4-n-propylcyclohexyl)-benzyl-(2-chloro-4-n-butyloxyphenyl)ether,
4-(trans-4-n-butylcyclohexyl)-benzyl-(2-fluoro-4-n-propylphenyl)ether,
4-(trans-4-ethylcyclohexyl)-benzyl-(2-fluoro-4-n-butylphenyl)ether,
4-(trans-4-n-pentylcyclohexyl)-benzyl-(2-fluoro-4-ethoxyphenyl)ether,
4-(trans-4-ethylcyclohexyl)-benzyl-(2-fluoro-4-n-pentyloxyphenyl)ether,
4-(trans-4-n-butylcyclohexyl)-benzyl-(2-cyano-4-n-butylphenyl)ether,
4-(trans-4-n-butylcyclohexyl)-benzyl-(2-cyano-4-ethylphenyl)ether,
4-(trans-4-n-hexylcyclohexyl)-benzyl-(2-cyano-4-n-propyloxyphenyl)ether,
4-(trans-4-n-heptylcyclohexyl)-benzyl-(4-ethoxyphenyl)thioether,
4-(trans-4-n-butylcyclohexyl)-benzyl-(4-n-pentyloxyphenyl)thioether,
4-(trans-4-n-pentylcyclohexyl)-benzyl-(4-n-butylphenyl)ethioether,
4-(trans-4-methylcyclohexyl)-benzyl-(4-n-hexylphenyl)thioether,
4-(trans-4-n-butylcyclohexyl)-benzyl-(4-fluorophenyl)thioether,
4-(trans-4-n-pentylcyclohexyl)-benzyl-(4-chlorophenyl)thioether,
4-(trans-4-ethylcyclohexyl)-benzyl-(4-bromophenyl)thioether
4-(trans-4-n-butylcyclohexyl)-benzyl-(4-cyanophenyl)thioether,
4-(trans-4-n-propylcyclohexyl)-benzyl-(4-cyanophenyl)thioether,
4-(trans-4-ethylcyclohexyl)-benzyl-(4-cyanophenyl)thioether,
4-(trans-4-ethylcyclohexyl)-benzyl-(2-fluoro-4-n-butyloxyphenyl)thioether
4-(trans-4-n-heptylcyclohexyl)-benzyl-(2-fluoro-4-ethylphenyl)thioether,
4-(trans-4-methylcyclohexyl)-benzyl-(2-fluoro-4-n-pentylphenyl)thioether,
4-(trans-4-n-propylcyclohexyl)-benzyl-(2-chloro-4-n-propylphenyl)thioether,
4-(trans-4-n-butylcyclohexyl)-benzyl-(2-chloro-4-n-propyloxyphenyl)thioether,
4-(trans-4-n-hexylcyclohexyl)-benzyl-(2-bromo-4-methylphenyl)thioether,
4-(trans-4-ethylcyclohexyl)-benzyl-(2-bromo-4-n-hexyloxyphenyl)thioether,
4-(trans-4-n-butylcyclohexyl)-benzyl-(2-cyano-4-n-propylphenyl)thioether,
4-(trans-4-n-butylcyclohexyl)-benzyl-(2-cyano-4-n-butyloxyphenyl)thioether, and
4-(trans-4-n-pentylcyclohexyl)-benzyl-(2-cyano-4-methoxyphenyl)thioether.

EXAMPLE 8

(a) To a Grignard solution prepared from 23.6 g of 4-(trans-4-ethylcyclohexyl)-benzyl chloride and 2.5 g of magnesium in 35 ml of diethyl ether there is added dropwise, with stirring, a solution of 21 g of 4-n-hexyloxybenzaldehyde in 35 ml of diethyl ether. The reaction mixture is further heated to the boil for 2 hours and, after cooling, hydrolyzed by the addition of 20 g of ice. The precipitate thereby formed is dissolved by the dropwise addition of aqueous 10% hydrochloric acid, the organic phase is then separated off, washed with water and evaporated. The residue is heated to the boil in 200 ml of toluene with 0.5 g of p-toluene-sulphonic acid on a water separator until no more water is separated. After cooling, the toluene solution is washed with 5% aqueous sodium hydrogen carbonate solution and water, dried over sodium sulphate and evaporated. The 4-(trans-4-ethylcyclohexyl)-4'-n-hexyloxystilbene remaining behind is recrystallized from ethanol; yield 31.5 g.

(b) Hydrogen is passed at room temperature into a suspension of 1 g of palladium-charcoal (5% Pd) in a solution of 20 g of 4-(trans-ethylcyclohexyl)-4'-n-hexyloxystilbene in 200 ml of toluene until cessation of the hydrogen uptake. Subsequently, the catalyst is filtered off, the filtrate is evaporated and the 1-[4-(trans-4-ethylcyclohexyl)-phenyl]-2-(4-n-hexyloxyphenyl)-ethane remaining behind is recrystallized from ethanol; yield: 19.6 g.

There are prepared analogously:
1-[4-(trans-4-n-butylcyclohexyl)-phenyl]-2-(4-n-heptyloxyphenyl)-ethane,
1-[4-(trans-4-n-butylcyclohexyl)-phenyl]-2-(4-n-pentyloxyphenyl)-ethane,
1-[4-(trans-4-n-propylcyclohexyl)-phenyl]-2-(4-n-butyloxyphenyl)-ethane,
1-[4-(trans-4-n-butylcyclohexyl)-phenyl]-2-(4-n-propyloxyphenyl)-ethane,
1-[4-(trans-4-n-hexylcyclohexyl)-phenyl]-2-(4-ethoxyphenyl)-ethane,
1-[4-(trans-4-n-hexylcyclohexyl)-phenyl]-2-(4-methoxyphenyl)-ethane,
1-[4-(trans-4-n-pentylcyclohexyl)-phenyl]-2-(4-ethoxyphenyl)-ethane,
1-[4-(trans-4-ethylcyclohexyl)-phenyl]-2-(4-n-butyloxyphenyl)-ethane, and
1-[4-(trans-4-methylcyclohexyl)-phenyl]-2-(4-n-hexyloxyphenyl)-ethane.

EXAMPLE 9

(a) To a suspension of 16 g of aluminum chloride in 13 ml of dichloromethane is added at −5°, with stirring, a solution of 21.4 g of 4-n-butylphenylacetic acid chloride in 8 ml of dichloromethane. After 30 minutes, a solution of 20.2 g of 4-(trans-4-n-propylcyclohexyl)-benzene in 46.5 ml of dichloromethane is added dropwise to this reaction mixture in such a manner that the temperature of the reaction mixture does not increase above 0°. Subsequently, it is further stirred for one hour at 0° and the reaction mixture then poured into a mixture of 250 g of ice and 75 ml of 35% aqueous hydrochloric acid. The organic phase is separated off, washed neutral with water, dried over sodium sulphate and evaporated. The 2-(4-n-butylphenyl)-4'-(trans-4-n-propylcyclohexyl)- acetophenone remaining behind is recrystallized from ethanol; yield 23.7 g.

(b) Hydrogen is passed into a suspension of 0.5 g of palladium-charcoal (5% Pd) in a solution of 7 g of 2-(4-n-butylphenyl)-4'-(trans-4-n-propylcyclohexyl)-acetophenone in 200 ml of ethanol at 35° until cessation of the take-up of hydrogen. Subsequently, the catalyst is filtered off, the filtrate is evaporated and the residue is recrystallized from petroleum ether (boiling range 40°-60°); yield 6.2 g.

1-[4-(trans-4-n-propylcyclohexyl)phenyl]-2-(4-n-butylphenyl)-ethane.

There are prepared analogously:
1-[4-(trans-4-n-hexylcyclohexyl)-phenyl]-2-(4-methylphenyl)-ethane,
1-[4-(trans-4-n-pentylcyclohexyl)-phenyl]-2-(4-ethylphenyl)-ethane,
1-[4-(trans-4-n-pentylcyclohexyl)-phenyl]-2-(4-n-propylphenyl)-ethane,
1-[4-(trans-4-n-butylcyclohexyl)-phenyl]-2-(4-ethylphenyl)-thane,
1-[4-(trans-4-n-butylcyclohexyl)-phenyl]-2-(4-n-butylphenyl)-ethane,
1-[4-(trans-4-n-butylcyclohexyl)-phenyl]-2-(4-n-pentylphenyl)-ethane,
1-[4-(Trans-4-n-propylcyclohexyl)-phenyl]-2-(4-n-butylphenyl)-ethane,
1-[4-(trans-4-ethylcyclohexyl)-phenyl]-2-(4-n-heptylphenyl)-ethane,
1-[4-(trans-4-methylcyclohexyl)-phenyl]-2-(4-n-hexylphenyl)-ethane,
1-[4-(trans-4-n-propylcyclohexyl)-phenyl]-2-(4-bromophenyl)-ethane,
1-[4-(trans-4-n-hexylcyclohexyl)-phenyl]-2-(4-chlorophenyl)-ethane,
1-[4-(trans-4-ethylcyclohexyl)-phenyl]-2-(4-fluorophenyl)-ethane,
1-[4-(trans-4-n-butylcyclohexyl)-phenyl]-2-(4-fluorophenyl)-ethane, and
1-[4-(trans-4-n-pentylcyclohexyl)-phenyl]-2-(4-fluorophenyl)-ethane.

EXAMPLE 10

Analogously to Example 4(b), 1-[4-(trans-4-n-propylcyclohexyl)-phenyl]-2-(4-bromophenyl)-ethane is reacted with copper(I) cyanide in pyridine/N-methylpyrrolidone to give 1-[4-(trans-4-n-propylcyclohexyl)-phenyl]-2-(4-cyanophenyl)-ethane; m.p. 36°.

There are prepared analogously:
1-[4-(trans-4-n-heptylcyclohexyl)-phenyl]-2-(4-cyanophenyl)-ethane, and
1-[4-(trans-4n-butylcyclohexyl)-phenyl]-2-(4-cyanophenyl)-ethane.

The following Examples concern the use in accordance with this invention of the compounds of formula I as components of liquid crystalline dielectrics.

EXAMPLE 11

A dielectric of
19% 4-(trans-4-n-propylcyclohexyl)-benzonitrile,
29% 4-(trans-4-n-pentylcyclohexyl)-benzonitrile,
20% 4-(trans-4-n-heptylcyclohexyl)-benzonitrile,
12% trans-4-n-pentyl-(4'-cyanobiphenylyl-4)-cyclohexane,
20% 1-[4-(trans-4-n-propylcyclohexyl)-phenyl]-2-(4-n-butylphenyl)-ethane has a clear point of 76° C., a threshold voltage in the twisted nematic cell of 1.8 V (20° C.) and possesses a viscosity of 24 cSt at 20° C.

EXAMPLE 12

A dielectric of
19% 4-(trans-4-n-propylcyclohexyl)-benzonitrile,
28% 4-(trans-4-n-pentylcyclohexyl)-benzonitrile,
11% trans-4-n-pentyl-(4'-cyanobiphenyl-4)-cyclohexane,
10% 4-(trans-4-n-propylcyclohexyl)-benzoic acid (4-propylphenyl)-ester
12% 4-(trans-4-n-propylcyclohexyl)-benzoic acid (trans-4-n-propylcyclohexyl)-ester and
20% 1-[4-(trans-4-n-propylcyclohexyl)-phenyl]-2-(4-n-butylphenyl)-ethane has a clear point of 91° C., a threshold voltage of 2.0 V (at 20° C.) and a viscosity of 32 cSt at 20° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyclohexylphenyl of the formula

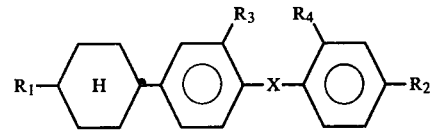

wherein X is —CH$_2$—CH$_2$—, —CH$_2$—O—, —CH$_2$—S—, —O—CH$_2$— or —S—CH$_2$—; R$_1$ is alkyl of up to 8 carbon atoms; R$_2$ is alkyl or alkoxy each of up to 8 carbon atoms, fluorine, chlorine, bromine or cyano; and R$_3$ and R$_4$ are both hydrogen or one is hydrogen and the other is fluorine, chlorine, bromine or cyano, with the proviso that R$_3$ and R$_4$ are both hydrogen when X is —CH$_2$—CH$_2$— or R$_2$ is fluorine, chlorine, bromine or cyano.

2. A compound of claim 1, of the formula

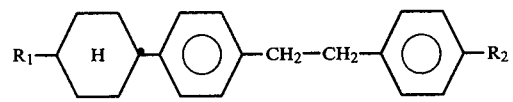

wherein R$_1$ and R$_2$ are as defined in claim 1.

3. A compound of claim 1, of the formula

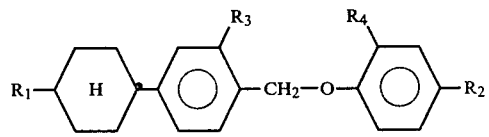

wherein R$_1$ to R$_4$ are as defined in claim 1.

4. A compound of claim 1, of the formula

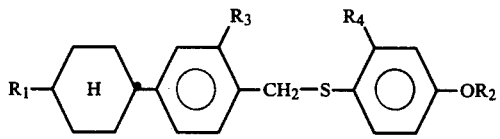

wherein $R_1$ to $R_4$ are as defined in claim 1.

5. A compound of claim 1, of the formula

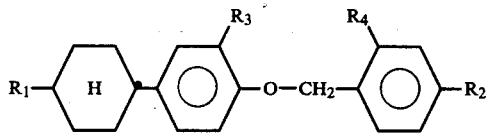

wherein $R_1$ to $R_4$ are as defined in claim 1.

6. A compound of claim 1, of the formula

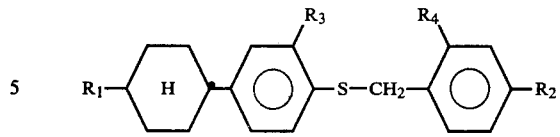

wherein $R_1$ to $R_4$ are as defined in claim 1.

7. A liquid crystalline dielectric for an electro-optical indicator element, comprising at least two liquid crystalline components at least one of which is a cyclohexylphenyl derivative of claim 1.

8. A liquid crystalline dielectric for an electro-optical indicator element, comprising at least two liquid crystalline components, at least one of which is a cyclohexylphenyl derivative of claim 1 in an amount of at least 5 wt % based on the total weight of the dielectric.

9. An electro-optical indicator element based on a liquid crystal cell containing a liquid crystalline dielectric of claim 7.

10. A compound of claim 1 wherein $R_2$ is F, Cl or Br.

11. A compound of claim 1 wherein $R^2$ is alkyl or alkoxy.

* * * * *